United States Patent
Chung et al.

(12) 
(10) Patent No.: US 6,268,187 B1
(45) Date of Patent: *Jul. 31, 2001

(54) PROCESS FOR PREPARING LYSOPHOSPHOLIPID USING ENZYME

(75) Inventors: Guk Hoon Chung, Yongin; Sun Ki Kim, Seoul; Joon Shick Rhee, Taejeon; Jeong Joon Han, Seoul, all of (KR)

(73) Assignee: Doosan Corporation, Seoul (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/119,395

(22) Filed: Jul. 21, 1998

(30) Foreign Application Priority Data

Jul. 24, 1997 (KR) .................................................. 97-34735

(51) Int. Cl.[7] ................................. C12P 13/00; C12P 7/64
(52) U.S. Cl. ............................ 435/128; 435/134; 435/135
(58) Field of Search .................................... 435/134, 135, 435/128

(56) References Cited

U.S. PATENT DOCUMENTS

| 5,126,155 | | 6/1992 | Palta et al. . |
| 5,137,660 | * | 8/1992 | Mazur .................................. 435/134 |
| 5,449,613 | | 9/1995 | Dordick et al. . |

OTHER PUBLICATIONS

Svensson, et al., *JAOCS*, 69:10, Oct. 1992, pp. 986–991.
Mutua, et al., *JAOCS*, 70:2, Feb. 1993, pp. 125–128.
Sarney, et al., *JAOCS*, 71:1, Jan. 1994, pp. 93–96.
Ghosh, et al., *JAOCS*, 74:6, 1997, pp. 761–763.
Svensson, et al., *Biotechnology*, 1990, pp. 255–258.
Yagi, et al., *J. of Fermentation and Bioengineering*, 69:1, 1990, pp. 23–25.
Han, et al., *Biotechnology Letters*, 17:5, May 1995, pp. 531–536.

* cited by examiner

*Primary Examiner*—Irene Marx
(74) *Attorney, Agent, or Firm*—Kenyon & Kenyon

(57) ABSTRACT

The present invention relates to a process for preparing lysophospholipid using enzyme, more specifically, a process for preparing lysophospholipid from glycerol-3-phosphate derivative using lipase based upon esterification or transesterification reaction.

9 Claims, 2 Drawing Sheets

PROCESS FOR PREPARING LYSOPHOSPHOLIPID USING ENZYME

BACKGROUND OF THE INVENTION

1. Field of the Invention

The present invention relates to a process for preparing lysophospholipid using enzyme, more specifically, a process for preparing lysophospholipid from glycerol-3-phosphate derivative using lipase based upon esterification or transesterification reaction.

2. Description of Prior Art

Phospholipids from natural sources contain several fatty acids, and their proportion depends on the source and fraction methods. For some practical applications, it is required to have phospholipids that contain specific fatty acid. In this case, chemical synthesis of phospholipid may be a promising approach. However, chemical methods for preparing phospholipids have many drawbacks. Very toxic and expensive solvents being employed should be removed, especially if the products are intended for food or pharmaceutical use. Further, substrates should be protected, deprotected and/or modified for preparing stereospecific phospholipid.

Lysophospholipid is the deacylated phospholipid at sn-1 or sn-2 position of glycerol backbone. Lysophospholipid is a surface active agent and used as emulsifier of food or cosmetics due to its high safety (Sarney, D. B., Fregapane, G., and Vulfson, E. N *J. Ant. Oil. Chenz. Soc.* 1994, 71, 93; Palta, J. P. and Farag, K. M. U.S. Pat. No. 5,126,155, 1992). Recently, lots of researches as to its biological properties have been carried out to apply this lysophospholipid to medical use (Buckalew, J. V. and Rauch, A. L. U.S. Pat. No. 4,7466,52, 1988).

Chemical synthesis of lysophospholipids requires not a few steps for protecting and deprotecting the substrate. Slotboom et. al. (Slotboom ,A. J., de Haas, G. H., and van Deenen, L. L. M. *Chem. Phys. Lipids* 1967 1, 317) prepared rac-1-stearyl lysophospholipid starting rac-1-stearyl-2-benzyl-3-iododeoxyglycerol. They used benzyl or trityl groups to protect the free hydroxyl group of glycerol and the blocking group was removed by the hydrogenolysis. This process was very complex and undesirable side-products were formed. Otherwise, the phospholipid having two fatty acids esterified with two hydroxyl groups has been prepared as by-product. Therefore, many attempts have been carried out to prepare lysophospholipid in biological method. The desired phospholipid with specific fatty acid which synthesized by chemical method or obtained by the fractionation of natural phospholipids were hydrolyzed by phospholipase A2 to corresponding lysophospholipid.

In the case of lysophophatidic acid (LPA) synthesis, it was more complex. LPA had to be prepared enzymatically either from the hydrolysis of lysopholipid by phospholipase D, or from the hydrolysis of phosphatidic acid by phosphatidic acid specific phospholipase A2 (Van Corven, E J., Van Rijswijk, A., Jalink, K., Van Der Bend, R. L., Van Blitterijk, W. J., and Moolenaar, W. H. *Biochein. J.* 1992, 281. 163). Calcium ion is required as a cofactor and should be controlled for efficient phospholipase A2 reaction.

Many lipase (EC-3.1.1.3.) have broad substrate specificity. Although natural substrates for the lipases are triglycerides, many of these enzymes have been used for breaking and forming of ester bonds in a wide varieties of compounds. There have been many reports on the modifications of phospholipids by lipase. Svensson et. al. (Svensson ,I., Adlercreutz, P., and Mattiasson, B. *Applied Microbiol. Biotechnol.* 1990, 33, 255) and Yagi et. al.(Yagi, T., Nakanishi, T., Yoshizawa Y., and Fukui F. *J. Fennent. Bioeng.* 1990, 69,23) investigated the transesterification of phosphatidylcholine with lipase. The lysophospholipid synthesis by lipase in a continuous reactor by transesterification was reported by Sarney et al.(1990). The inventors reported that lysophosphatidic acid (LPA) could be synthesized from glycerol-3-phosohate(G-3-P) with free fatty acid by lipase-catalyzed esterification in a solvent-free system. (Han, J. J. and Rhee, J. S. *Biotechnol. Lett.* 1995, 17, 531). A method for the production of lysophospholipid is characterized by the esterification of 1-hydroxyl group of glycerophospholipid by microbial, plant or animal lipase. Preferably, 12–22 saturated or unsaturated fatty acid is used at a concentration of 0.2–5.0 mol, preferably 0.5–2.0 mol on 1 mol of glycerophospholipid. In both case, water content control was the one of most important factor on the synthesis yield.

The water level of the reaction system is an important factor because it affects the equilibrium of esterification reaction. Water is formed during biocatalytic esterification. An organic reaction mixture may be characterized by a single water activity ($a_w$) value instead of water content or concentration. In the case of water being a reactant in the desired conversion or side reaction, $a_w$ reactant determines the water mass action effect on the position of equilibrium. Many reports confirmed that the continuous control of $a_w$ during biocatalysis in organic media can increase yield and reaction rate.

Kahn et al. (Kahn, S. A., Halling, J. P. and Bell, G. *Enzyme Microb. Technol.* 1990, 12, 453) adjusted the $a_w$ of headspace above the reaction medium by circulation of head space gas through a drying column. The aluminum oxide sensor was used for continuous monitoring and control of $a_w$ during the lipase-catalyzed esterification.: however, the sensor has many limitations in stability, sensitivity, and measurement range. Another $a_w$ control method is to perform the reaction in a vessel with saturated salt solution in contact with the reaction mixture via the gas phase, so that the saturated salt solution continuously absorbs and releases water vapor to keep the $a_w$ constant. Svensson et al. (1993) developed a unique method for an $a_w$ control. A saturated salt solution was slowly circulated inside a silicon tubing which was contacted with traction medium, so that water vapor can be transported through the wall of the tubing, and thus the a. in the reaction medium can thereby be continuously controlled. In this system, however, the transport rate and equilibrium through the tubing was very slow and the apparatus was somewhat complex.

Another way for the continuous $a_w$ control is the use of salt hydrate pair. It was reported that a salt hydrate pair can control the water level in the reaction mixture by taking up or releasing water as required to keep a constant $a_w$ condition during the reaction (Halling, J. P. *Biothehnol. Tech.* 1992, 6, 271). Each kind of salt hydrate pair has a typical $a_w$. When a hydrated salt and its corresponding lower hydrate or anhydrous form are present together, ideal behavior implies a fixed equilibrium water vapor pressure and hence a constant $a_w$, whatever the relative quantities of the two forms.

The present invention developed the biosynthetic process for preparing lysophospholipid using lipase in a convenient process without protecting substrate. we also controlled the $a_w$ of the reaction medium by using a salt hydrate pair in order to increase the reaction rate and yield.

SUMMARY OF THE INVENTION

An object of the present invention is to provide a process for preparing lysophospholipid using lipase comprising the steps of:

i) mixing and dissolving the glycerol-3-phosphate derivative represented by formula (II) and fatty acid derivative represented by formula (III);
ii) reacting said mixture with lipase selected from the group consisting of lipase M (Mucor javanicus), *Candida cylindracia* (or *Candida rugosa*) lipase, lipase D (*Rhizopus delemar*) and lipozyme (*Mucor miehei*);
iii) extracting the reaction mixture; and
iv) obtaining the lysophospholipid represented by formula (I)

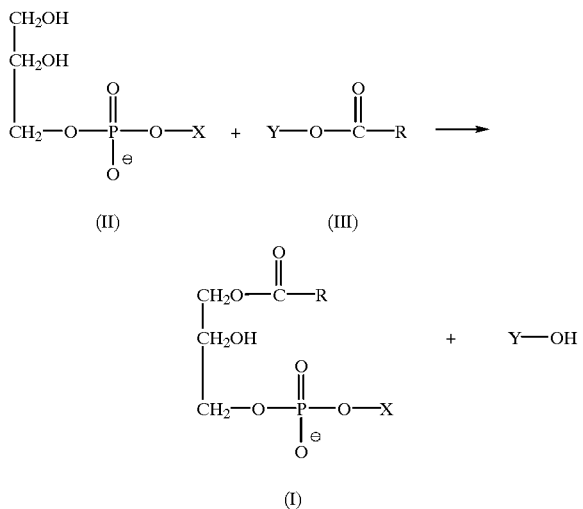

wherein
R is $C_6$–$C_{23}$ alkl or alkenyl having one or more double bond;
X is a choline, glycerol, serine or ethanolamine;
Y is a hydrogen atom, $C_1$–$C_6$ alkyl, $C_1$–$C_6$ alkenyl or compounds represented by following formula (A)

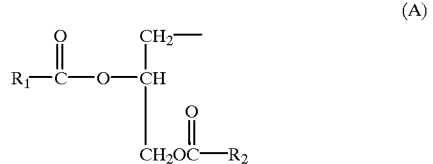

in which
$R_1$ and $R_2$ are each independently $C_6$–$C_{23}$ alkyl or alkenyl having one or more double bond.

The further object of present invention is to provide a method further comprising recovering lysophospholipids formed in the reaction mixture in the extraction step with solvents, especially, acetone.

The further object of present invention is to provide a method further comprising addition of salt hydrate pair to the reaction mixture; wherein said salt hydrate pair is one or more selected from the group consisting of $NaB_4O_7$. $10H_2O$—$NaB_4O_7.5H_2O$, $Na_4P_2O_7$. $10H_2O$—$Na_4P_2O_7$ anhydrous, $NaBr$. $2H_2O$—$NaBr$ anhydrous, $CH_3COONa$. $3H_2O$—$CH_3COONa$ anhydrous, $NaI$. $2H_2O$—$NaI$ anhydrous and $LiSO_4.1H_2O$—$LiSO_4$ anhydrous.

The further object of present invention is to provide a method further comprising addition of organic solvent to the reaction mixture; wherein said organic solvent is one or more selected from the group consisting of acetonitrile, N,N'-dimethylformamide, dioxane, 2-butanol, diethylether, pentane, hexane, cyclohexane, heptane, isooctane, octane, butyl acetate and ethyl acetate.

The further object of present invention is to provide a method further comprising addition of organic solvent and salt hydrate pair to the reaction mixture; wherein said organic solvent is one or more selected from the group consisting of acetonitrile, N,N'-dimethylformamide, dioxane, 2-butanol, diethylether, pentane, hexane, cyclohexane, heptane, isooctane, octane, butyl acetate and ethyl acetate; wherein said salt hydrate pair is one or more selected from the group consisting of $NaB_4O_7.10H_2O$—$NaB_4O_7$. $5H_2O$, $Na_4P_2O_7$. $10H_2O$—$Na_4P_2O_7$ anhydrous, $NaBr$. $2H_2O$—$NaBr$ anhydrous, $CH_3COONa$. $3H_2O$—$CH_3COONa$ anhydrous, $NaI$. $2H_2O$—$NaI$ anhydrous and $LiSO_4.1H_2O$—$LiSO_4$ anhydrous.

The further object of present invention is to provide a method further comprising addition of organic solvent and small amount of water to the reaction mixture; wherein said organic solvent is one or more selected from the group consisting of acetonitrile, N,N'-dimethylformamide, dioxane, 2-butanol, diethylether, pentane, hexane, cyclohexane, heptane, isooctane, octane, butyl acetate and ethyl acetate; wherein the water is added to reaction system in an amount of 0.01–20 wt %, preferably, 0.1–5 wt % as to total weight of reactant.

DETAILED DESCRIPTION OF THE INVENTION

Figure 1:
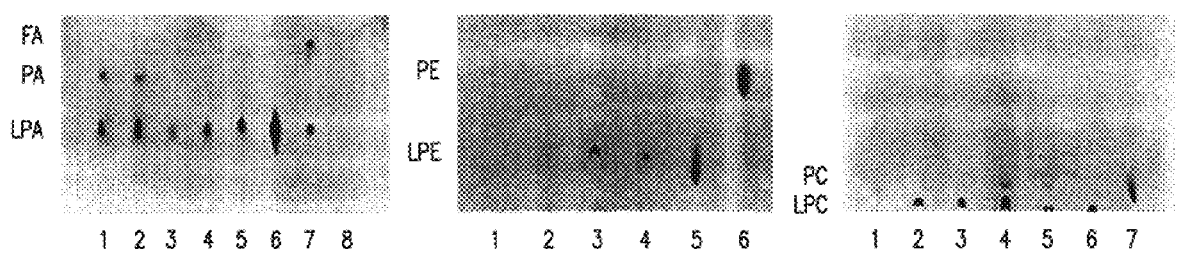
FIG. 1 shows the TLC analytical results of lysophospholipid prepared by the method according to this invention.
Figure 2A:
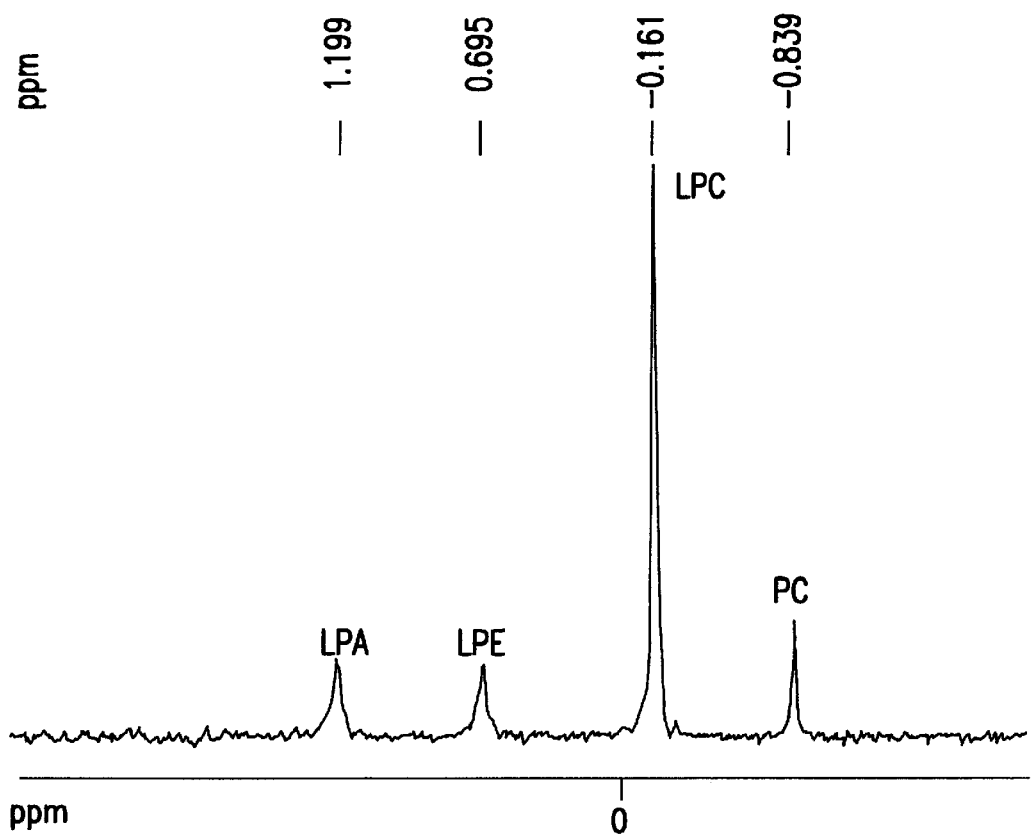
FIG. 2 shows the $^{31}P$ spectrum of lysophosphatidyl choline (LPC), lysophosphatidic acid (LPA) and lysophosphatidylethanolamine (LPE) standard (a), and lysophosphatidylethanolamine (LPE) prepared by the method according to this invention(b).
Figure 2B:
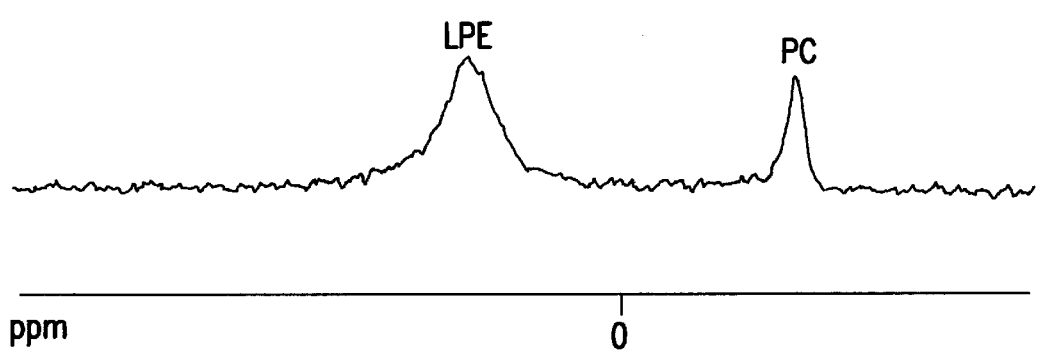

Lysophospholipids were synthesized by the lipase-catalyzed esterification of glycerophosphoryl backbone with fatty acid. The reaction was started with mixing and dissolving the glycerol-3-phosphate derivative (II) and fatty acid derivative (III) with lipase. The synthetic activity of lipase could be affected by water activity, solubility of substrate, kinds of substrate, enzyme amount, and so on. In present invention, we found the optimal reaction condition of lipase for the synthesis of lysophospholipids.

Salt hydrate pair is very useful for controlling the water content of reaction system. It is important to control the water content of the reaction system by following reasons. The water is one of products of this esterification reaction. Therefore, to proceed this reaction, the water has to be removed. However, the low water content causes the decline of enzyme activity. To solve above conflict problem, the direct addition of salt hydrate pair to reaction media makes the control of water content (or water activity, $a_w$). Salt hydrate pair can control the water activity to maintain the water condition by absorption or releasing of water. If the direct addition of salt hydrate in the reaction mixture may cause some problems like toxic effect on the reaction product, direct addition is not desirable. In this case, salt hydrate pair is laid on the head space of the reactor to induce the optimal water activity of the reaction system, which prevents the toxicity of salt hydrate pair. The desirable salt hydrate pair is one or more selected from the group consisting of $NaB_{4O7}$. $10H_2O$—$NaB_4O_7.5H_2O$, $Na_4P_2O_7$. $10H_2O$—$Na_4P_2O_7$ anhydrous, $NaBr$. $2H_2O$—$NaBr$ anhydrous, $CH_3COONa$. $3H_2O$—$CH_3COONa$ anhydrous, $NaI$. $2H_2O$—$NaI$ anhydrous and $LiSO_4.1H_2O$—$LiSO_4$ anhydrous.

Some free fatty acid or its ester could play a role as a reaction solvent, but also as a substrate. In this case we adapted the solvent-free reaction system for the esterification. Organic solvents were used for the solubilization of hardly soluble substrate. The desirable organic solvent is one or more selected from the group consisting of acetonitrile, N,N'-dimethylformamide, dioxane, 2-butanol, diethylether, pentane, hexane, cyclohexane, heptane, isooctane, octane, butyl acetate and ethyl acetate.

On the other hand, it is possible to add water to the reaction system. The amount of water added to reaction system is 0.01–20 wt %, preferably, 0.1–5 wt % as to total weight of reactant. In case of adding the water to the reaction system, the lysophospholipid may be obtained without adding salt hydrate pair. However, in this case, it is not easy to control the water activity in the reaction system.

The lipase used for this invention is one or more selected from the group consisting of lipase M (*Mucor javanicus*), *Candida cylindraeea* (or *Candida rugosa*) lipase, lipase D (*Rhizopus delemar*) and lipozyme (*Mucor miehei*). Among them, lipozyme is desirable. Lipozyme can be used as commercially marketed without further purification or immobilization.

In order to obtain high purity lysophospholipid, the end products of the reaction are extracted with chloroform: methanol: water (65: 25: 4. by volume) solution. After removal of all solid materials by filtration, the solvent phase was dried under the vacuum Acetone was used for the removal of unreacted fatty acid derivatives from the lysophospholipids. Upon addition of acetone, lysophospholipids precipitates out of solution, and may be further purified by any art-standard process like silica gel chromatography.

The present invention can be explained more concretely by following examples. However, the terms and expressions which have been employed are used as terms of description and not of limitation, and scope of this invention cannot be construed to be limited by following examples. It is recognized that various modifications are possible within the scope of invention.

[The analysis of produced lysophospholipid]
1. TLC Analysis
   TLC plate:TLC plate (20×20 cm) silica gel 60 $F_{254}$ (Merck Co.)
   Developing solution
      (1) Analysis for lysophosphatidic acid chloroform::methanol:acetic acid:water=50:30:4:4
      (2) Analysis for lysophosphatidyl choline and lysophosphatidyl ethanolamine chloroform:acetone:methanol:acetic acid:water=6:8:2:2:1
   Coloring solution:molybdenum blue
2. HPLC Analysis
   (1) Analysis of Lysophosphatidic acid
      HPLC Analyzer:Pump:Younglin M930
         Detector:Alltech Varex MKIII ELSD Detector
         Column:Hypersil silica column (250×4.6 mm)
   (2) Analysis of Lysophosphatidyl choline
      HPLC Analyzer:Pump:Younglin M930
         Detector:Alltech Varex MKIII ELSD Detector
         Column:YMC—$NH_2$
   (3) Analysis of Lysophosphatidyl ethanolamine
      HPLC Analyzer:Pump:Younglin M930
         Detector:Alltech Varex MKIII ELSD Detector
         Column:Hypersil silica column (250×4.6 mm)

EXAMPLE 1

Synthesis of Lysophospholipids in Open System

Given amounts of glycerol-3-phosphate derivative (II) and fatty acid derivative(III) were mixed vigorously by a magnetic stirrer in an open reactor. 0.1 g of Lypozyme (Novo Nordisk) was added and the reaction was carried out at 50° C. and 300 rpm for 48 hours. The produced lysophospholipids was analyzed by HPLC.

TABLE 1

Yields of lysophospholipids in open reactor.

| Substrate | | | | | |
|---|---|---|---|---|---|
| glycerol-3-phosphate derivative (II), | | fatty acid derivative (III) | | | |
| substance | amount (mmol) | substance | amount (mmol) | Product | Yields (%) |
| G-3-PC | 1.5 | capric acid | 10 | lyso-PC | 28.4 |
| G-3-PC | 1.5 | triolein | 3 | lyso-PC | 20.4 |
| G-3-PC | 1.5 | capryl methyl ester | 10 | lyso-PC | 12.1 |
| G-3-PE | 1.5 | capric acid | 10 | lyso-PE | 5 |
| G-3-PE | 1.5 | triolein | 3 | lyso-PE | 3.2 |
| G-3-PE | 1.5 | capryl methyl ester | 10 | lyso-PE | 4.2 |

Abbreation:
G-3-PC: glycerol-3-phosphorylcholine,
G-3-PE: glycerol-3-phosphorylethanolamine
lyso-PC: lysophosphatidylcholine
lyso-PE: lysophosphatidylethanolamine

EXAMPLE 2

Synthesis of Lysophospholipid in Closed System

Given amounts of glycerol-3-phosphate derivative (II) and fatty acid derivative(III) were mixed in 20 mL of acetonitrile vigorously by a magnetic stirrer in a closed reactor. 0.1 g of Lypozyme (Novo Nordisk) was added and the reaction was carried out at 50° C. and 300 rpm for 48 hours. The produced lysophospholipids was analyzed by HPLC.

TABLE 2

Yields of lysophospholipids in closed reactor.

| Substrate | | | | | |
|---|---|---|---|---|---|
| glycerol-3-phosphate derivative (II), | | fatty acid derivative (III) | | | |
| substance | amount (mmol) | substance | amount (mmol) | Product | Yields (%) |
| G-3-PC | 1.5 | capryl methyl acid | 10 | lyso-PC | 12.1 |
| G-3-FE | 1.5 | tricaprin | 3 | lyso-PE | 4.1 |
| G-3-PE | 1.5 | soybean oil | 3 g | lyso-PE | 2.5 |

Abbreviation
G-3-PC: glycerol-3-phosphorylcholine,
G-3-PE: glycerol-3-phosphorylethanolamine
lyso-PC: lysophosphatidylcholine
lyso-PE: lysophosphatidylethanolamine

EXAMPLE 3

Synthesis of Lysophosphatidylcholine in Closed System With Water Activity Control 1.5 mmol of glycerol-3-phosphorylcholine (G-3-PC) and 3.0 mmol of capric acid were mixed vigorously by a magnetic stirrer in closed reactor. 0.1 g of Lypozyme (Novo Nordisk) together with the addition of salt hydrate pairwas added for the water activity control and the reaction was carried out at 50° C. and 300 rpm for 48 hours. The salt hydrate pair used in this example is one or more selected form the group consisting of $NaB_4O_7.10H_2O$—$NaB_4O_7.5H_2O$, $Na_4P_2O_7.10H_2O$—$Na_4P_2O_7$ anhydrous, $NaBr.2H_2O$—$NaBr$ anhydrous, $CH_3COONa.3H_2O$—$CH_3COONa$ anhydrous, $NaI.2H_2O$—$NaI$ anhydrous and $LiSO_4.1H_2O$—$LiSO_4$. 0.2 g of salt hydrate pair with an equal amount of each hydrate form was added. The produced lysophosphatidyl choline was analyzed by HPLC. The yield of produced lysophosphatidyl choline was described in Table 3.

TABLE 3

Yields of lysophosphatidylcholine with water activity control.

| Water activity | Salt hydrate pair | Yields of lysophosphatidylcholine (%) |
|---|---|---|
| 0.12 | $LiSO_4.1/0H_2O$ | 5.2 |
| 0.17 | $NaI.2/0H_2O$ | 7.4 |
| 0.37 | $CH_3COONa.3/0H_2O$ | 14.2 |
| 0.46 | $NaBr.2/0H_2O$ | 13.2 |
| 0.60 | $Na_4P_2O_7.10/0H_2O$ | 36.2 |
| 0.80 | $NaB_4O_7.10/5H_2O$ | 5.0 |

EXAMPLE 4

Synthesis of Lysophosphatidylethanolamine in Closed System With Water Activity Control 1.5 mmol of glycerol-3-phosphorylethanolamine (G-3-PE) and 3.0 mmol of capric acid were mixed vigorously by a magnetic stirrer in closed reactor. 0.1 g of Lypozyme (Novo Nordisk) together with the addition of salt hydrate pairwas added for the water activity control and the reaction was carried out at 50° C. and 300 rpm for 48 hours. The salt hydrate pair used in this example is one or more selected form the group consisting of $NaB_4O_7.10H_2O$—$NaB_4O_7.5H_2O$, $Na_4P_2O_7.10H_2O$—$Na_4P_2O_7$ anhydrous, $NaBr.2H_2O$—$NaBr$ anhydrous, $CH_3COONa.3H_2O$—$CH_3COONa$ anhydrous, $NaI.2H_2O$—$NaI$ anhydrous and $LiSO_4.1H_2O$—$LiSO_4$. 0.2 g of salt hydrate pair with an equal amount of each hydrate form was added. The produced lysophosphatidylethanolamine was analyzed by HPLC. The yield of produced lysophosphatidylethanolamine was described in Table 4.

TABLE 4

Yields of Lysophosphatidylethanolamine with water activity control.

| Water activity | Salt hydrate pair | Yields of lysophosphatidylethanolamine (%) |
|---|---|---|
| 0.12 | $LiSO_4.1/0H_2O$ | 2.1 |
| 0.17 | $NaI.2/0H_2O$ | 1.9 |
| 0.37 | $CH_3COONa.3/0H_2O$ | 22.9 |
| 0.46 | $NaBr.2/0H_2O$ | 8.7 |
| 0.60 | $Na_4P_2O_7.10/0H_2O$ | 9.8 |
| 0.80 | $NaB_4O_7.10/5H_2O$ | 2.1 |

EXAMPLE 5

Synthesis of Lysophosphatidylcholine in Closed System Together With the Addition of Water and Organic Solvent 1.5 mmol of glycerol-3-phosphatidylcholine and 3 mmol of capric acid were mixed vigorously by a magnetic stirrer and dissloved in 20 mL of acetonitrile. 0.1 g of Lypozyme was added together with the addition of 0.1 ml water and the reaction was carried out at 50° C. and 300 rpm for 48 hours. The produced lysophosphatidylcholine was analyzed by HPLC. The yield of produced lysophosphatidylcholine was 15.9%.

EXAMPLE 6

Synthesis of Lysophosphatidylcholine in Closed System With Addition of Salt Hydrate Pair and Organic Solvents 1.5 mmol of glycerol-3-phosphatidyl choline and 3 mmol of capric acid were mixed and dissloved in 20 mL of acetonitrile. 0.1 g of Lypozyme together with the addition of salt hydrate pair was added and the reaction was carried out at 50° C. for 48 hours. The salt hydrate pair used in this example is one or more selected form the group consisting of $NaB_4O_7.10H_2O$—$NaB_4O_7.5H_2O$, $Na_4P_2O_7.10H_2O$—$Na_4P_2O_7$ anhydrous, $NaBr.2H_2O$—$NaBr$ anhydrous, $CH_3COONa.3H_2O$—$CH_3COONa$ anhydrous, $NaI.2H_2O$—$NaI$ anhydrous and $LiSO_4.1H_2O$—$LiSO_4$. 0.2 g of salt hydrate pair with an equal amount of each hydrate form was added. The produced lysophosphatidylcholine was analyzed by HPLC. The yield of produced lysophosphatidylcholine in $Na_4P_2O_7.10H_2O$—$Na_4P_2O_7$ anhydrous was 18.9%.

What is claimed is:

1. A method for preparing a lysophospholipid using lipase comprising the steps of;

i) forming a first mixture by mixing and dissolving a glycerol-3-phosphate derivative represented by formula (II) and a fatty acid derivative represented by formula (III) in the presence of one or more salt hydrate pairs selected from the group consisting of $NaB_4O_7.10H_2O$—$NaB_4O_7.5H_2O$, $Na_4P_2O_7.10H_2O$—$Na_4P_2O_7$ anhydrous, $NaBr.2H_2O$—$NaBr$ anhydrous, $CH_3COONa.3H_2O$—$CH_3COONa$ anhydrous, $NaI.2H_2O$—$NaI$ anhydrous and $LiSO_4.1H_2O$—$LiSO_4$ anhydrous in an amount effective to increase the reaction rate and yield of the reaction of a lipase selected from the group consisting of *Mucor javanicus* lipase M, *Candida cylindracea* lipase, *Candida rugosa* lipase, *Rhizopus delemar* lipase D and *Maucor miehei* lipozyme with the first mixture by controlling water activity ($a_w$);

ii) reacting said first mixture with a lipase selected from the group consisting of *Mucor javanicus* lipase M, *Candida cylindracea* lipase, *Candida rugosa* lipase; *Rhizopus delemar* lipase D and *Mucor miehei* lipozyme to form a reacted mixture;

iii) extracting said reacted mixture; and iv) recovering the lysophospholipid of formula (I)

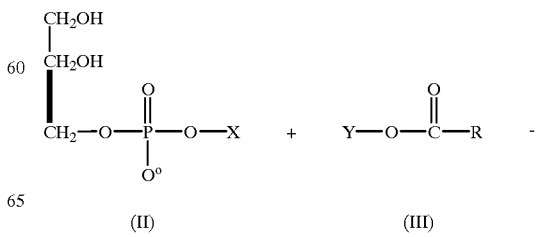

-continued

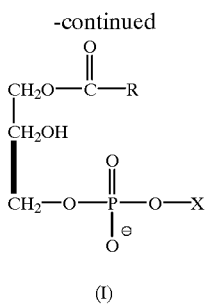

(I)

wherein

R is $C_6$–$C_{23}$ alkyl or alkenyl having one or more double bonds;

X is a choline, glycerol, serine or ethanolamice;

Y is a hydrogen atom, $C_1$–$C_6$ alkyl, $C_1$–$C_6$ alkenyl, or a compound of formula (A)

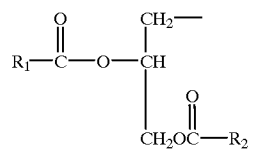

in which

R1 and R2 are each independently $C_6$–$C_2$, alkyl or alkenyl having one or more double bonds.

2. The method of claim 1, wherein said extraction of said reacted mixture is performed by extracting said reacted mixture with solvents.

3. The method of claim 2, further comprising extracting said reacted mixture with acetone following step (iii).

4. The method of claim 1, further comprising the step of adding organic solvent to said first mixture prior to or during the reaction with said lipase selected from the group consisting of *Mucor javanicus* lipase *M. Candida cylindracea* linase, *Candida rugosa* lipase, *Rhizopus delemar* lipase D and *Mucor miehei* lipozyme.

5. The method of claim 4, wherein said organic solvent is one or more selected from the group consisting of acetonitrile, N,N'-dimethylformamide, dioxane, 2-butanol, diethylether, pentane, hexane, cyclohexane, heptane, isooctane, octane, butyl acetate and ethyl acetate.

6. The method of claim 1, further comprising the step of adding organic solvent and a small amount of water to said first mixture prior to or during the reaction with said lipase selected from the group consisting of *Mucor javanicus* lipase *M. Candida cylindracea* lipase, *Candida rugosa* lipase, *Rhizopus delemar* lipase D and *Mucor miehei* lipozyme.

7. The method of claim 6, wherein said organic solvent is one or more selected from the group consisting of acetonitrile, N,N'-dimethylformamide, dioxane, 2-butanol, diethylether, pentane, hexane, cyclohexane, heptane, isooctane, octane, butyl acetate and ethyl acetate.

8. The method of claim 7, wherein said small amount of water is added to said first mixture in an amount of 0.01–20 wt % of said first mixture.

9. The method of claim 7, wherein said small amount of water is added to said first mixture in an amount of 0.1–5 wt % of said first mixture.

* * * * *